United States Patent [19]
Martinelli

[11] Patent Number: 5,592,939
[45] Date of Patent: Jan. 14, 1997

[54] METHOD AND SYSTEM FOR NAVIGATING A CATHETER PROBE

[76] Inventor: Michael A. Martinelli, 58 Wedgemere Ave., Winchester, Mass. 01890

[21] Appl. No.: 490,342

[22] Filed: Jun. 14, 1995

[51] Int. Cl.$^6$ .................................................. A61B 5/05
[52] U.S. Cl. .................................... 128/653.1; 128/899
[58] Field of Search ............................. 128/653.1, 899; 600/117

[56] References Cited

U.S. PATENT DOCUMENTS

| | | | |
|---|---|---|---|
| 3,439,256 | 4/1969 | Kahne | 323/51 |
| 3,674,014 | 7/1972 | Tillander | 128/2.05 |
| 3,868,565 | 2/1975 | Kuipers | 324/34 |
| 4,173,228 | 11/1979 | Van Steenwyk et al. | 128/653 |
| 4,317,078 | 2/1982 | Weed et al. | 324/208 |
| 4,339,953 | 7/1982 | Iwasaki | 73/654 |
| 4,422,041 | 12/1983 | Lienau | 324/207 |
| 4,584,577 | 4/1986 | Temple | 340/870.32 |
| 4,642,786 | 2/1987 | Hansen | 364/559 |
| 4,719,419 | 1/1988 | Dawley | 324/208 |
| 4,821,731 | 4/1989 | Martinelli et al. | 128/662.06 |
| 4,849,692 | 7/1989 | Blood | 324/208 |
| 4,905,698 | 3/1990 | Strohl, Jr. et al. | 128/653 |
| 5,187,475 | 2/1993 | Wagener et al. | 340/870.32 |
| 5,211,165 | 5/1993 | Dumoulin et al. | 128/653.1 |
| 5,228,442 | 7/1993 | Imran | 128/642 |
| 5,253,647 | 10/1993 | Takahashi et al. | 128/653.1 |
| 5,425,367 | 6/1995 | Shapiro et al. | 128/653.1 |
| 5,425,382 | 6/1995 | Golden et al. | 128/899 |
| B1 4,905,698 | 10/1991 | Strohl et al. | 128/653 R |

FOREIGN PATENT DOCUMENTS

WO94/04938 3/1994 WIPO.

*Primary Examiner*—Marvin M. Laeef
*Assistant Examiner*—Eleni Mantis Mereader
*Attorney, Agent, or Firm*—Lappin & Kusmer LLP

[57] ABSTRACT

A system for navigating a catheter probe through a body cavity includes a sensing coil affixed to a distal end of the probe. Magnetic fields are projected into the body cavity to induce voltage signals in the sensing coil that are sufficient to describe the orientation and position of the probe. A set of magnetic coils each generates a substantially uniform field in a single respective dimension. The orientation angles of the sensing coil may be determined from known values of the unidirectional fields and the measured induced voltage signals. Gradient magnetic fields with components in two dimensions are projected into the body cavity to induce another group of voltage signals. The geometrical intersection of constant voltage surfaces developed by certain gradient fields that produce the measured induced voltage signals is a set of lines on which the catheter is located. The point of intersection of such lines yields the positional coordinates.

22 Claims, 6 Drawing Sheets

METHOD AND SYSTEM FOR NAVIGATING A CATHETER PROBE

FIELD OF THE INVENTION

The present invention relates to catheter navigation systems and, more particularly, to a method and system for determining the position and orientation of a catheter probe being used during a surgical procedure.

BACKGROUND OF THE INVENTION

Various configurations have been proposed to guide and detect a catheter probe through the internal spaces of a patient undergoing a surgical procedure. These proposed configurations are characterized by several alternative approaches including, inter alia, procedures for solving equations to determine unknown location parameters, the generation and detection of magnetic fields, and the use of sensing devices affixed to the catheter probe.

U.S. Pat. No. 4,905,698 to Strohl, Jr. et al. discloses a locator device external to a subject for generating an electromagnetic field that projects into the subject. A catheter inserted into the subject is fitted with a sensing coil at its distal end. The phase of the voltage that is induced in the coil in response to the field is compared to the phase of the generated field. When an in-phase condition occurs, this is an indication that the locator is behind the coil; alternatively, an out-of-phase condition indicates that the locator is beyond the coil. Positions intermediate these two rough approximations of the coil position are not determined other than by a beeping indicator that signifies that this intermediate positioning has been reached.

U.S. Pat. No. 4,821,731 to Martinelli et al. discloses an electroacoustical transducer means secured to the distal end of a catheter that is inserted into a subject for generating acoustical pulses that propagate along an imaging axis and reflect from an anatomical area of interest. The acoustic echoes are converted by the transducer means into electrical signals representative of an image of the anatomical area under reflection and the relative position of the transducer means and angular orientation of the sensing/imaging axis.

U.S. Pat. No. 4,642,786 to Hansen discloses a magnetic position and orientation measurement system that determines the location of an object in space with various configurations, each characterized by the attachment of a retransmitter to the object consisting of passive resonant circuits. The retransmitter is in a predetermined position and orientation with respect to the object. A magnetic field is generated at a resonant frequency of the retransmitter which then retransmits a magnetic field for subsequent reception. The position and orientation of the object may be calculated based upon the induced signals as developed by the reception of the retransmitted magnetic field. The original transmission and reception may be implemented with an integrated transceiver, separate transmitter and receiver elements, or a single transmitter and an array of receiver coils.

U.S. Pat. No. 4,317,078 to Weed et al. discloses how the location of a magnetically sensitive element may be determined by moving a magnetic field source along specified reference axes to induce signals in the sensor so as to identify a set of null points representative of certain flux linkage values. The null point locations are used to calculate the sensor position.

U.S. Pat. No. 3,868,565 describes a system where a magnetic field is generated which rotates about a known pointing vector. The generated field is sensed along at least two axes by a sensor attached to the object to be located or tracked. Based upon the relationship between the sensed magnetic field components, the position of the object relative to the pointing vector can be computed.

U.S. Pat. No. 4,173,228 to Van Steenwyk et al. discloses a catheter locating system that includes a sensor attached to the distal end of the catheter. An electromagnetic field is projected into the body cavity with magnetic probe coils. The field is detected by the sensor, which generates an induced signal whose magnitude and phase are representative of field strength, separation of sensor and probe coils, and relative orientation of sensor and probe coils. The probe coil undergoes linear and rotational movement to identify orientations and locations of the probe coil where minima and maxima occur in the measured signal induced in the sensor. This information is representative of the position and orientation of the sensor.

U.S. Pat. No. 5,211,165 to Dumoulin et al. discloses a modified catheter device that includes a small RF transmit coil attached to its distal end. The transmit coil is driven by an RF source to create an electromagnetic field that induces electrical signals in an array of receive coils distributed around a region of interest. Alternatively, the receive coils can be placed on the invasive device and the transmit coils are distributed outside the patient. A minimum of one transmit coil and three receive coils is necessary to precisely determine the location of the invasive device. A series of equations is developed to solve for the unknowns x-y-z-$\phi$-$\theta$.

PCT Application No. WO94/04938 to Bladen et al. describes how the location and orientation of a single sensing coil may be determined from induced signals developed in response to a sequence of applied magnetic fields emanating from three groups of field generators each including three mutually orthogonal coils.

The positioning methodology developed by Bladen et al. involves calculating the distance from the sensing coil to each group of field generators as a function of the induced voltage developed in the sensing coil by the field generator. The distance calculation is used to define the radius of a sphere centered on the respective field generator. The intersection (i.e., overlap) of the spheres is used to calculate an estimate of the sensor position, using the spherical radius extending from the known location of the field generators as the estimate for each generator.

The orientation algorithm of Bladen et al. develops general equations for induced voltage including the entire set of unknown variables (x-y-z location and $\phi$-$\theta$ orientation). The algorithm specifically solves for the orientation parameters by substituting the measured induced voltage and the computed x-y-z coordinates into the general induced voltage equation, and then reduces the equations to the unknown variables $\phi$-$\theta$.

In an alternative orientation algorithm described by Bladen et al., the induced voltage is treated as a vector quantity, allowing the angle between the magnetic field at the generator and the radial vector joining the sensor to the generator to be calculated with a dot product computation. The angle between the radial vector and the sensor axis can be determined from the computed field angle using the dipole equations that define the generator fields. This sensor angle and the radial position as determined by the position algorithm together define the sensor position for use in the alternative orientation algorithm. These values are used to compute the angular orientation $\phi$ and $\theta$.

OBJECTS OF THE INVENTION

It is a general object of the present invention to obviate the above-noted and other disadvantages of the prior art.

It is a more specific object of the present invention to provide a catheter navigation system capable of determining the location of a catheter probe.

It is a further object of the present invention to develop a catheter navigation system employing a sensing coil affixed to the end of a catheter probe for generating induced voltage signals that are sufficient to describe the position and orientation of the sensing coil.

It is a further object of the present invention to develop a methodology for generating magnetic fields that are sufficient to create a series of soluble mathematical expressions describing the position and orientation of the sensing coil.

SUMMARY OF THE INVENTION

In one aspect of the present invention, an improved method of determining the location of a magnetically-sensitive, electrically conductive sensing coil affixed to a distal end of a catheter probe partially inserted into a body cavity within a navigational domain comprises the steps of:

inducing within said sensing coil a set of orientation signal values each representative of an orientation of said sensing coil and independent of a position of said sensing coil;

determining the orientation of said sensing coil using said induced orientation signal values;

inducing within said sensing coil a set of positional signal values each representative of the position of said sensing coil; and determining the position of said sensing coil using said positional signal values and said determined orientation.

In another aspect of the present invention, an improved system for determining the location of a magnetically-sensitive, electrically conductive sensing coil affixed to a distal end of a catheter probe partially inserted into a body cavity within a navigational domain comprises:

first transmit means for projecting into said navigational domain magnetic energy that is sufficient to induce signal values within said sensing coil representative of an orientation of said sensing coil and independent of the position of said sensing coil;

second transmit means for projecting into said navigational domain magnetic energy that is sufficient to induce signal values within said sensing coil representative of the position of said sensing coil; and analysis means, coupled to said first transmit means and said second transmit means, for determining the position and orientation of said sensing coil from said induced signal values.

In another aspect of the present invention, an improved method of determining the location of a magnetically-sensitive, electrically conductive sensing coil affixed to a distal end of a catheter probe partially inserted into a body cavity within a navigational domain comprises the steps of:

defining the location of said sensing coil with a set of independent location parameters; and sequentially generating within said navigational domain a sequence of magnetic fields for inducing within said sensing coil a corresponding sequence of induced signals each defined by an induced signal expression that functionally relates said induced signal to certain ones of said location parameters, such that said set of location parameters is determinable by sequentially solving individual signal expression groups each including certain ones of said induced signal expressions and sufficient to represent a subset of said location parameters.

BRIEF DESCRIPTION OF THE DRAWINGS

Throughout the drawings the same or similar elements are identified by the same reference numeral.

DETAILED DESCRIPTION OF THE PREFERRED EMBODIMENTS

The present invention is directed to a method and system for determining the location of a catheter or endoscopic probe inserted into a selected body cavity of a patient undergoing a surgical procedure. The location data is obtained from electrical measurements of voltage signals that are induced within a sensing coil affixed to the distal end of the catheter probe. These induced voltage signals are generated by the sensing coil in response to prespecified electromagnetic fields that project into the anatomical region of interest which contains all prospective locations of the catheters probe. The electrical measurements of the induced signals provide sufficient information to compute the angular orientation and the positional coordinates of the sensing coil, and hence the catheter probe, which collectively define the location of the sensing coil. The present invention is operative as the patient is disposed on a patient-supporting examination deck.

As used herein, "sensing coil" refers to an electrically conductive, magnetically sensitive element that is responsive to time-dependent magnetic fields for generating induced voltage signals as a function of and representative of the applied time-dependent magnetic field. The sensing coil is adaptable for secure engagement to the distal end of a catheter probe.

As used herein, "navigational domain" refers to a fully enclosed spatial region whose internal volume substantially encloses the complete prospective range of movement of the sensing coil. The navigational domain may be defined by any geometrical space but preferably takes the form of a spherical volume. Under surgical operating conditions, the navigational domain will correspond to an anatomical region of the recumbent patient where surgical viewing or investigation is desired (e.g., a diseased area of tissue or an organ).

As used herein, "last navigational point" (hereinafter "the LNP") refers to the most recently determined location of the sensing coil before another iteration of the location algorithm is performed.

As used herein, "uniform field" refers to a magnetic field having a large magnetic field component in a specified axial dimension and relatively smaller magnetic field components in the other axial dimensions, and characterized by substantially uniform field values throughout the navigational domain. In the x-y-z coordinate system used herein, where the uniform fields of interest are the x-directed, y-directed, and z-directed fields, the induced voltage signals developed by such fields in the sensing coil are designated $V_x$, $V_y$, and $V_z$, respectively. The term "undirectional field" is used interchangeably with "uniform field" when appropriate.

As used herein, "undirectional coils" refer to a magnetic assembly that is operative to generate a uniform field (as defined above) within the navigational domain. A distinct magnetic assembly is employed for each uniform field. Although the unidirectional coils described herein are preferably implemented with a collection of appropriately designed magnetic coils, this implementation should not be construed as a limitation of the present invention. Rather, the unidirectional coils may be constructed from any magnetic configuration that is sufficient to generate the uniform fields.

As used herein, "gradient field" refers to a time-dependent magnetic field having non-zero field components (i.e., components with a high spatial gradient) in two of the three axial dimensions for the coordinate system of interest (e.g., x-y-z system), and a substantially zero component in the remaining axial dimension. For mathematical purposes, a substantially zero component is generated when its value is small compared to the net vector resulting from the other two field components.

As used herein, "constant signal surface" or "constant voltage surface" refers to a surface contour along which at every possible point of location for the sensing coil the same induced voltage is developed in the sensing coil.

As used herein, "delta coils" refer to a magnetic assembly for generating a gradient field (as defined above) within the navigational domain. As will become more apparent hereinafter, the delta coils will typically be described in the context of delta coil pairs including a long coil set and a short coil set each generating gradient fields with components in the same axial dimensions but whose magnetic field patterns are different. Each of the long and short coil sets may be considered to generate a family of constant signal or constant voltage surfaces from the sensing coil within the navigational domain. Although the delta coils are preferably implemented with an array of appropriately designed magnetic coils (discussed below), this preferred implementation should not serve as a limitation of the present invention as it should be apparent to those skilled in the art that other magnetic configurations may be used to adequately generate the gradient fields.

As used herein, "magnetic look-up-table" (alternatively referenced as "the LUT") refers to a database including the magnetic field values at every x-y-z coordinate position within the navigational domain for the unidirectional coils and delta coils used by the present invention. Accordingly, input data consisting of an x-y-z coordinate and a magnetic field identifier, which designates a selected magnetic coil assembly, is indexed within the database to a corresponding set of magnetic field values constituting the output data. For the x-y-z coordinate system, the output data is represented by the magnetic field variables $H_x$ $H_y$ $H_z$ where the subscript indicates the axial dimension along which the magnetic field value is being reported. The database is created through a computational analysis of the magnetic field patterns generated by the magnetic coil configurations used herein. The mathematical model to develop the necessary formulae defining the field patterns may be developed, for example, from near field electromagnetic theory. An instructive text for facilitating such an analysis is "Field and Wave Electromagnetics" 2nd edition Addison Wesley (1989) by D. K. Cheng, herein incorporated by reference. The database may be stored in any type of facility including, inter alia, read-only memory, firmware, optical storage, or other types of computer storage. Additionally, the database information may be organized into any type of format such as a spreadsheet. It should be apparent to those skilled in the art that any suitable technique may be used to ascertain or record the magnetic field values for the magnetic coil assemblies used herein.

Separation of Variables Methodology

The mathematical construct underlying the present invention is a methodology termed separation of variables. In accordance with this methodology, appropriate equations are developed to isolate unknown variables in such a manner that renders the equations uniquely soluble. There are five unknown variables ($\phi$-$\theta$-x-y-z) that define the location and orientation of the sensing coil. A typical approach to solving for these variables would be to develop a series of coupled non-linear equations expressing the relationship among the variables. However, these equations are generally not uniquely soluble, i.e., multiple solutions are possible.

The mathematical approach used herein and predicated on the separation of variables concept is directed to the development of a series of signal expression statements functionally relating induced voltage values to certain ones of the unknown location parameters. The relationships defined by these expression statements (i.e., induced voltage equations) are such that the unknown variables are determinable by sequentially solving the expression statements. In accordance with one aspect of the present invention, a class of special magnetic fields is generated with characteristic spatial structuring and shaping that is sufficient to cause the variables (i.e., the location parameters) to separate within these induced voltage equations so as to permit resolution of the parameters x-y-z-$\phi$-$\theta$ when the equations are sequentially solved.

In particular, a series of substantially uniform fields is successively generated in the x-, y-, and z-directions with the group of unidirectional coils, thereby developing induced voltage expressions (discussed below) involving only the variables $\phi$ and $\theta$ independent of the unknown positional variables x-y-z. This uncoupling of the variables $\phi$-$\theta$ from the variables x-y-z as accomplished by the substantially uniform fields is specifically evident in the three induced voltage equations expressed in two unknowns (i.e., $\phi$ and $\theta$), which are easily soluble.

The separation of variables methodology as applied to the determination of the unknown positional coordinates x-y-z is implemented with a sequence of gradient fields as generated by an appropriate group of delta coils. Since the gradient fields have components in only two of the axial dimensions, these fields induce voltages in the sensing coil that are dependent upon the magnetic field values in only these two dimensions at the sensing coil position. As a result, each gradient field generates a family of constant signal surfaces from the sensing coil, from which a constant signal surface is identified for each gradient field that produces the measured induced voltage in the sensing coil. The intersection of two such constant signal surfaces is a line along which the catheter is located. This intersection line is defined by an expression in two of the unknown positional coordinates, wherein the other equation parameters are known, i.e., the measured induced voltage values, the magnetic field values at every x-y-z coordinate for the coil groups (as supplied by the LUT), and the as-computed $\phi$-$\theta$ orientation. If an appropriate delta coil configuration is used (e.g., three delta coil pairs), an appropriate number of such intersection lines (e.g., three) may be produced to sufficiently and uniquely resolve the x-y-z coordinates (e.g., by calculating the intersection of such three intersection lines).

Since there are five unknown variables to completely define the catheter probe location, an equal number of independent equations are needed to sufficiently describe its location. These unknowns may be determined using one coil and five magnetic fields (as described herein), two coils and three magnetic fields, or three coils and two magnetic fields.

Overview of Location Algorithm

In accordance with the present invention, a location algorithm was developed for determining the location of a sensing coil affixed to the distal end of a catheter probe that is navigated through an anatomical region of interest within a recumbent patient. The location of the sensing coil is defined by an angular orientation and positional coordinates. The angular orientation is represented by an angle $\phi$ corresponding to the angle of departure from the z-axis and an angle $\theta$ corresponding to the angle between the x-axis and the projection onto the x-y plane of the vector coincident with the longitudinal axis of the coil. In the coordinate system for describing the present invention, the z-axis coincides with the longitudinal dimension extending from the patient's head to foot. The x-axis coincides with a lateral dimension across the patient's body, and the y-axis is perpendicular to the planar top of the pallet or examination deck. These dimensions are identified as the patient is disposed in the recumbent position on the pallet. As discussed below, the angular orientation is determined from signals induced in the sensing coil in response to a sequence of substantially uniform, unidirectional fields generated successively within the navigational domain. The positional coordinates are determined from signals induced in the sensing coil in response to the gradient magnetic fields.

By way of background, the time-dependent magnetic fields projected into the navigational domain induce voltages in the coil that are representative of the orientation of the coil axis relative to the lines of magnetic flux. The development of an induced voltage in an electrical conductor in response to a changing magnetic field is defined by Faraday's law. If one considers any closed stationary path in space which is linked by a changing magnetic field, it is found that the induced voltage $V_{ind}$ around this path is equal to the negative time rate of change of the total magnetic flux through the closed path. Denoting a closed path with the variable C, the magnetic flux through C is given by, $$\Psi = \int_s B \cdot dS$$

where S is any surface bounded by the closed path C. Thus, the mathematical statement of Faraday's law is $$V_{ind} = -\frac{\delta}{\delta t} \int_s B \cdot dS$$

Basically, the law states that a changing magnetic field will induce an electric field which exists in space regardless of whether a conducting wire is present. If a conducting wire is present in the electric field, an induced voltage will develop in the conductor. For a single-turn coil of wire of radius d located in a uniform magnetic field $B=B_o \sin\omega t$, where the axis of the sensing coil is displaced at an angle $\theta$ with respect to the lines of magnetic flux, the induced voltage measured between the two open ends of the coil is expressed as:

$$V_{ind} = -\frac{\partial}{\partial t}\int_s B \cdot dS = -\frac{\partial}{\partial t}(\pi d^2 B_o \cos\theta \sin\omega t)$$

$$V_{ind} = -\omega\pi d^2 B_o \cos\theta \cos\omega t$$

This relationship for a single coil may be used to determine the induced voltage within a coil of N turns. Assuming that each turn of the coil is separately and equally linked by the magnetic flux (e.g., in tightly wound coils), the induced voltage within the entire coil assembly may be approximated as the summation of the induced voltages developed in each turn. Accordingly, the total voltage across the entire coil assembly is N times the induced voltage for a single turn; hence, the induced voltage $V_{ind}$ is equivalent to $$V_{ind} = -N\omega\pi d^2 B_o \cos\theta\cos\omega t$$

Clearly, the induced voltage in the sensing coil will vary with changes in the angular orientation between the coil axis and the direction of the magnetic field lines.

A useful reference frame for spatially conceptualizing the interaction between the sensing coil and the magnetic fields is the Cartesian coordinate system defined by mutually perpendicular axes x-y-z. For purposes of illustration, a nonzero vector $\hat{a}$ is selected to coincide with the axis through the sensing coil of the present invention (hereinafter "coil axis").

The angles $\alpha$, $\beta$, and $\gamma$ that the vector $\hat{a}$ makes with the unit coordinate vectors $\hat{i}$, $\hat{j}$, and $\hat{k}$, respectively, are called the direction angles of $\hat{a}$; the trigonometric terms $\cos\alpha$, $\cos\beta$, and $\cos\gamma$ represent direction cosine values. Employing vector product notation, the following expressions are developed: $\hat{a}\cdot\hat{i}=\|\hat{a}\|\cos\alpha$; $\hat{a}\cdot\hat{j}=\|\hat{a}\|\cos\beta$; and $\hat{a}\cdot\hat{k}=\|\hat{a}\|\cos\gamma$. Referencing the induced voltage equations set forth above, these angles $\alpha$, $\beta$ and $\gamma$ correspond to the angular displacement of the coil axis with respect to uniform fields generated along the x-axis, y-axis, and z-axis directions, respectively. Thus, the correspondence between direction cosine expressions is as follows:

cosα corresponds to sinφcosθ;

cosβ corresponds to sinθsinφ; and cosγ corresponds to cosφ.

Accordingly, the following relationships illustrate the dependence of induced voltage on the orientation parameters φ and θ:

$V_x \approx \sin\phi\cos\theta$;

$V_y \approx \sin\theta\sin\phi$; and $V_z \approx \cos\phi$, where the subscript indicates the direction of the magnetic field that produced the measured induced voltage.

Figure 4:
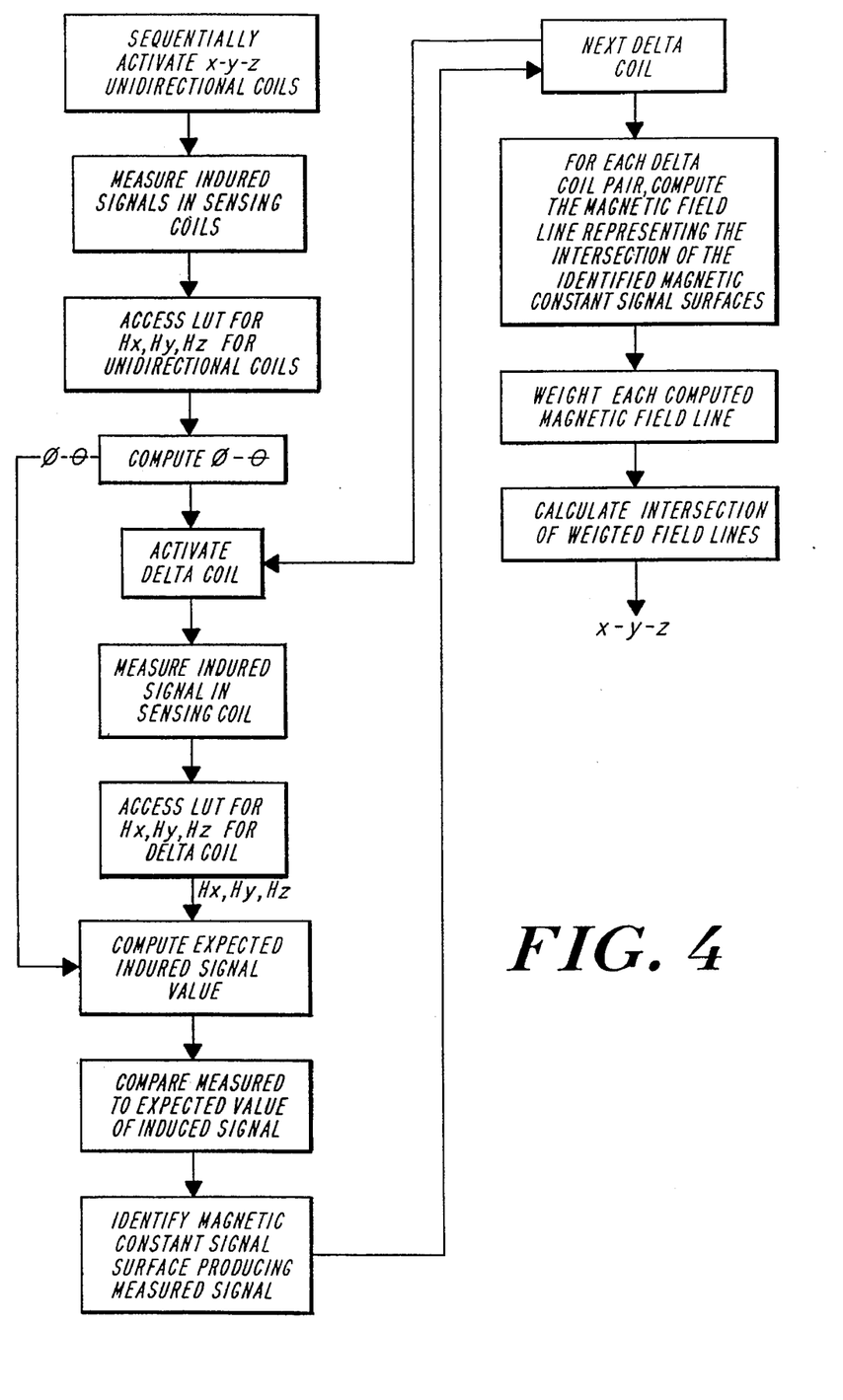
FIG. 4 is a flow diagram describing the location algorithm in accordance with the present invention.

FIG. 4 is a flowchart detailing the location algorithm according to the present invention and should be referenced in connection with the discussion below.

As noted above, the last navigation point (LNP) refers to the x-y-z positional coordinates of the sensing coil as determined by the immediately previous computation cycle of the algorithm. For the first cycle, the LNP is the center of the viewing field.

In accordance with a preferred embodiment of the present invention for implementing the location algorithm, a magnetic assembly of nine individual coil sets are used to generate the magnetic fields sufficient to develop a corresponding set of nine induced voltage signals that are fully representative of the location of the sensing coil. The nine coil sets correspond to a group of three unidirectional coil sets for generating uniform fields in the x, y, and z-directions; a first delta coil group including a short coil set at 0° and a long coil set at 0°; a second delta coil group including a short coil set at 120° and a long coil set at 120°; and a third delta coil group including a short coil set at 240° and a long coil set at 240°. The angular designations associated with the delta coil groups indicate the angle with respect to the z-axis of the coil dimension that is perpendicular to the direction of elongation of the delta coils. Accordingly, the three delta coil groups are arranged pair-wise in a circular orientation about the y-axis at angles of 0°, 120°, and 240°.

The look-up-table (LUT) consists of a database containing the magnetic field values ($H_x$ $H_y$ $H_z$) at every x-y-z coordinate location within the navigational domain for five coil sets: the unidirectional coil sets for generating the uniform fields in the x, y, and z-directions; the short coil (SC) set at 0°; and the long coil (LC) set at 0°. The magnetic field value data for the short and long coil sets at 120° and 240° may be obtained from the LUT by rotating the field vectors for the long and short coil sets at 0° by the angle (i.e., ±120°) appropriate for the given coil set. The input data for the LUT consists of the x-y-z coordinates and a designation of which coil set is being used to generate the magnetic fields. In response to this input data, the LUT supplies the magnetic field values $H_x$ $H_y$ $H_z$ at the selected x-y-z coordinates for the designated coil set.

The LUT is present to speed up the operational sequence of the location algorithm. Otherwise, an undesirable computational delay exists if the required magnetic fields from the nine coil sets must be individually calculated during each iteration of the algorithm. By predetermining the magnetic field values and storing them in LUT, the location algorithm need only access the LUT to retrieve the appropriate field value without endeavoring into any complex field analysis. At x-y-z coordinates other than those for which magnetic field values are determined in the LUT, an interpolation procedure is employed to calculate the field value.

Determining Angular Orientation of the Sensing Coil

The location algorithm of the present invention initially undertakes a procedure to determine the angular orientation of the sensing coil. An assumption is first made that the coil orientation does not appreciably change during the period between cycle computations. Accordingly, the magnetic field values corresponding to the uniform field pattern at the LNP are used as an approximation for the magnetic field values at the current but as yet undetermined location.

The unidirectional coils are activated in succession, each generating a substantially uniform field that projects into the navigational domain and induces a corresponding voltage signal in the sensing coil. The induced voltage signals are measured by an appropriate detection unit coupled to a proximal end of the catheter device where an electrical connection to the sensing coil is established via suitable connection means extending along the body of the catheter device.

The LUT is then accessed three times to acquire the magnetic field values at the LNP for each of the three unidirectional coils. These values and the measured voltage signals are then substituted into the appropriate equations set forth below to solve for the unknown variables φ and θ that define the coil orientation.

As a general principle, the voltage induced within the sensing coil may be resolved into components along each of the axial dimensions as determined by the extent to which the magnetic flux density is developed along these axial dimensions. For example, a general formula for the induced voltage produced by the unidirectional coil which generates a substantially uniform field in the x-direction is as follows:

$$V_x = H_{xx}K \sin\phi\cos\theta + H_{yx}K \sin\phi\sin\theta + H_{zx}K \cos\phi$$

where magnetic field intensity H is related to magnetic flux density by $B = \mu H$ and $K = \mu_o \bar{\omega} N \pi d^2$. The first subscript in the field intensity term indicates the axial dimension along which the magnetic field value was determined by accessing the LUT for the given coil set at the LNP, while the second subscript indicates the field-generating coil set. For an x-directed substantially uniform field, the terms $H_{yz}$ and $H_{zx}$ are small compared to $H_{xx}$. Similar equations are developed below for the induced voltages produced by the unidirectional coils successively generating a y-directed and z-directed substantially uniform field:

$$V_y = H_{xy}K \sin\phi\cos\theta + H_{yy}K \sin\phi\sin\theta + H_{zy}K \cos\phi,$$

and $$V_z = H_{xz}K \sin\phi\cos\theta + H_{yz}K \sin\phi\sin\theta + H_{zz}K \cos\phi.$$

The terms $H_{xy}$ and $H_{zy}$ in the equation for $V_y$ and the terms $H_{xz}$ and $H_{yz}$ in the equation for $V_z$ are small compared to $H_{yy}$ and $H_{zz}$, respectively. After substituting the measured values for the induced voltage signals, the equations are simultaneously solved to determine the unknown variables φ and θ defining the orientation of the sensing coil.

Determining Positional Coordinates of the Sensing Coil

By way of summary, the procedure for determining the positional coordinates of the sensing coil in accordance with the present invention first involves activating each delta coil in succession and measuring the induced voltage thereby developed in the sensing coil. Next, the LUT is accessed to obtain the magnetic field values at the LNP for each specified delta coil. These magnetic field values and the as-computed values for the orientation angles $\phi$ and $\theta$ are then substituted into the appropriate induced voltage equations to calculate for each delta coil the expected value of the voltage signal induced in the sensing coil. This expected value of the induced signal corresponds to a specific and unique member of the family of constant signal surfaces of the delta coils.

Based on the difference between the measured and expected values for the induced voltage signals, a gradient is calculated (representative of the rate of change of the induced signal) that permits identification of the specific constant signal surface that is responsible for generating the measured value of the induced signal. This procedure is repeated for each delta coil.

For the activation of each delta coil group (comprised of one long coil set and one short coil set), there is an intersection line defined by the intersection of the two constant signal surfaces (which were identified as developing the measured induced signal) on which the sensing coil is located. The intersection of the three such lines from the three delta coil groups uniquely provides the x-y-z coordinates of the sensing coil. Although two such lines are sufficient to describe the position of the sensing coil, greater accuracy and more reliable performance in determining the catheter position is achieved with three lines.

The following is a more detailed discussion of the procedure summarized above for determining the positional coordinates.

The magnetic field pattern generated by the entire assembly of short coil and long coil sets is characterized by a family of surfaces of constant signal or constant voltage developed by the sensing coil, each having non-zero components in two of the axis directions and a small component in the remaining axis direction. For example, the magnetic field surfaces generated by the short and long coil sets oriented at 0° relative to the x-axis have a small value in the x-direction. The short coil positioned at 0° (i.e., SC(0°)) and long coil positioned at 0° (i.e., LC (0°)) are each independently activated. The induced voltage in the sensing coil is measured for each coil set. The LUT is then accessed to determine the magnetic field values for the SC(0°) and LC(0°) coil set at the LNP.

These magnetic field values (i.e., $H_x$=small and non-zero $H_y$, $H_z$ components) are used in conjunction with the as-computed orientation angles $\phi$ and $\theta$ to calculate the values of the induced catheter signals that would be expected from such magnetic field values. The expected and measured induced voltage values are compared, and the difference is used to identify the constant signal surface from each of the SC(0°) and LC(0°) coil sets that would have produced the measured induced signals. The intersection of these identified magnetic constant signal surfaces is a line parallel to the x-axis (thereby resolving the y-z coordinates).

The aforementioned procedure involving the long and short coils oriented at 0° is iteratively repeated for a long and short coil set oriented at 120° (i.e., SC(120°) and LC(120°)) and 240° (i.e., SC(240°) and LC(240°)).

More specifically, the coil sets SC(120°) and LC(120°) are sequentially activated to induce corresponding catheter signals in the sensing coil. In order to utilize the LUT data on the coil sets oriented at 0° for determining the magnetic field components at the LNP generated by the coil sets SC(120°) and LC(120°), a modified LNP is calculated that is equivalent to the original LNP rotationally displaced by 120°. The LUT is then accessed with the modified LNP to determine the magnetic field values generated by the SC(120°) and LC(120°) coil sets at the modified LNP. The field vectors produced by the LUT for both the long coil and short coil are then rotated (−120°) to go from the modified LNP to the actual LNP. Based upon these field values, a pair of induced catheter signals are calculated that correspond to the expected signal values arising from the magnetic field values for the SC(120°) and LC(120°) coil sets. The difference between the measured and expected induced catheter signals is used to identify the magnetic constant signal surface for each of the SC(120°) and LC(120°) coil sets that could produce the measured catheter signal. The intersection of these identified magnetic constant signal surfaces is a line oriented at 120° to the x-axis.

A similar procedure is used involving a modified LNP that is rotationally displaced 240° to simulate the magnetic field patterns for the SC(240°) and LC(240°) coil sets using the SC(0°) and LC(0°) field data. A line oriented at 240° to the x-axis is then identified along which the catheter is located.

Each of the field lines oriented at 0°, 120° and 240° to the x-axis is weighted according to the strength of the measured catheter signals. For example, a weak measurement indicates a relatively imprecise identification of the intersection line, resulting in a weaker weighting. This weighting reflects the accuracy of the estimation used to determine the location of the catheter with the specified coil set. An averaging technique is used to compute a weighted estimate of the intersection of the lines L(0°), L(120°) and L(240°). The intersection is the new value for x-y-z and will replace the x-y-z of the old LNP to become the next LNP. The algorithm iteratively repeats the aforementioned operations using the updated LNP to arrive at the location of the sensing coil after each computation cycle (e.g., every 0.1 s).

Magnetic Assembly for Determining Angular Orientation of Sensing Coil

Figure 1:
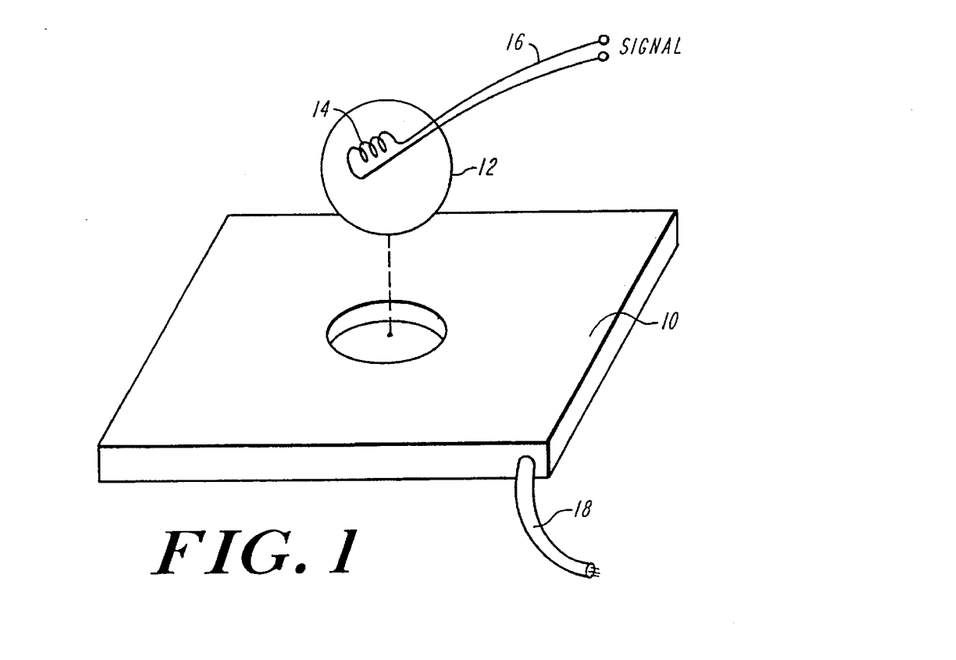
FIG. 1 schematically illustrates a perspective view of a patient-supporting examination deck in accordance with a preferred embodiment of the present invention.

FIG. 1 schematically illustrates a perspective view of an examination deck that facilitates implementation of the location algorithm in accordance with a preferred embodiment of the present invention, and which employs a magnetic coil assembly arranged in a flat configuration. The examination deck includes a planar top platform 10 suitable for accommodating a recumbent patient disposed lengthwise on the planar top. The navigational domain is illustratively depicted as the spherical volume 12 enclosing a sensing coil 14 attached via suitable connection means 16 to an external signal detection apparatus (not shown). The coil sets embedded in platform 10 (and described in connection with FIGS. 2A–C and 3) are activated by a signal drive unit (not shown) connected via line 18. The examination deck is preferably constructed from a suitable magnetically-permeable material to facilitate magnetic coupling between the embedded coil sets and the overlying sensing coil.

Coil Set for Generating X-Directed Field

Figure 2A:
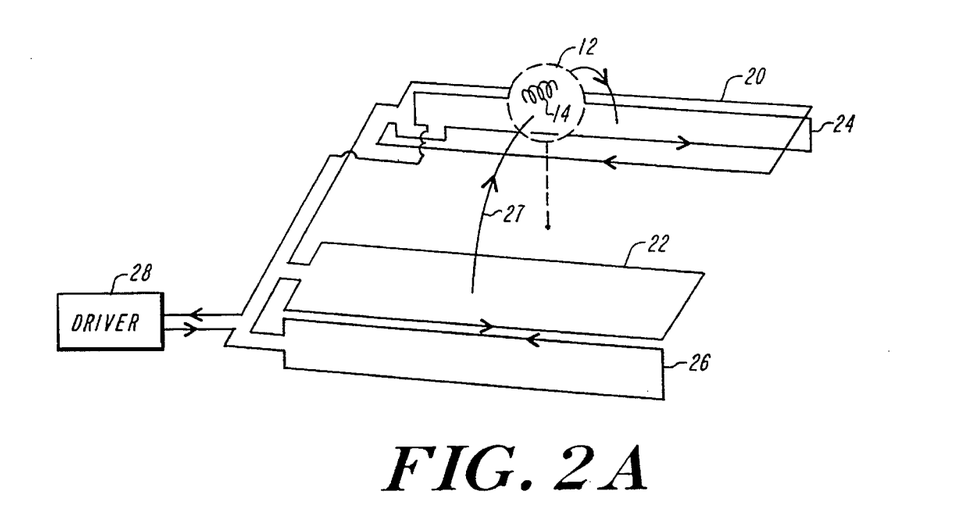
FIGS. 2A–C schematically illustrate a series of magnetic coil sets for generating uniform fields in the x-, y-, and z-directions, respectively, in accordance with a preferred embodiment of the present invention, and which are configured within the deck of FIG. 1.

FIG. 2A schematically illustrates the unidirectional coil set for generating a substantially uniform x-directed field throughout the navigational domain 12. The coil set includes a first coil pair with elements 20 and 24 and a second coil pair with elements 22 and 26, where the current flow as supplied by drive unit 28 is indicated by the arrow symbol. Coil elements 20 and 22 are disposed in the major surface of platform 10, while elements 24 and 26 are disposed in the lateral walls of platform 10. Elements 24 and 26 are preferably used as compensation coils to substantially cancel undesirable field components generated by elements 20 and 22 in the y- and z-directions. The coils cumulatively generate a substantially uniform x-directed field as indicated by representative field line 27.

Coil Set for Generating Y-Directed Field

Figure 2B:
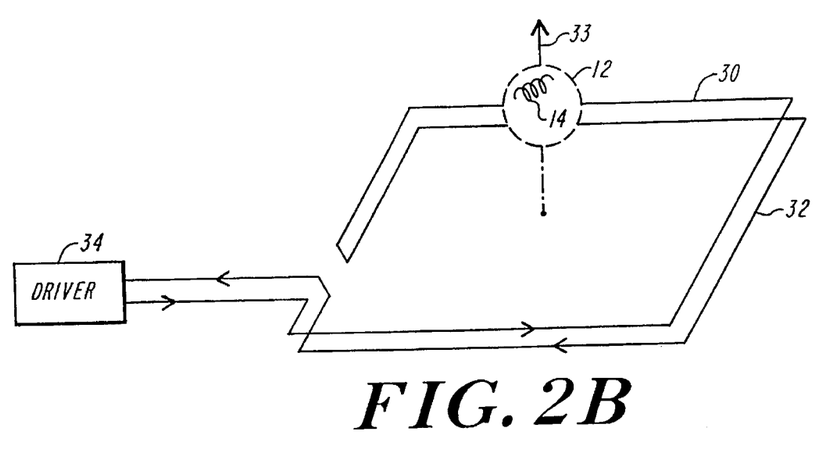

FIG. 2B schematically illustrates the unidirectional coil set for generating a substantially uniform y-directed field throughout the navigational domain 12. The coil set includes a coil pair with elements 30 and 32 disposed in spaced-apart and parallel relationship within platform 10, with the indicated current flow as supplied by drive unit 34. The coils generate a substantially uniform y-directed field as indicated by representative field line 33.

Coil Set for Generating Z-Directed Field

Figure 2C:
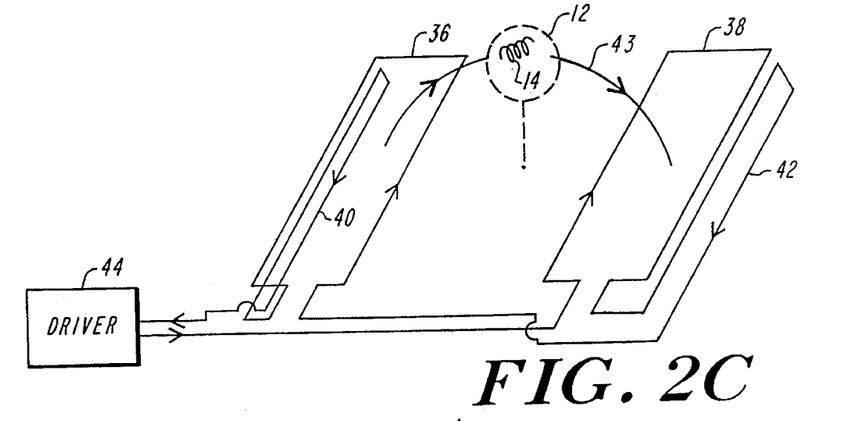

FIG. 2C schematically illustrates the unidirectional coil set for generating a substantially uniform z-directed field throughout the navigational domain 12. The coil set includes a first coil pair with elements 36 and 40 and a second coil pair with elements 38 and 42, with the indicated current flow as supplied by drive unit 44. Coil elements 36 and 38 are disposed in the major surface of platform 10, while elements 40 and 42 are disposed in the lateral walls of platform 10. Elements 40 and 42 are preferably used as compensation coils (e.g., Cunard coils) to substantially cancel undesirable field components generated by elements 36 and 38 in the x- and y-directions. The coils cumulatively generate a substantially uniform z-directed field as indicated by representative field line 43.

The coil configurations shown in the Figures are only illustrative and should not be construed as a limitation of the present invention, as it should be apparent to those skilled in the art that other coil configurations are possible within the scope of the present invention provided such other configurations produce the desired magnetic field patterns. A suitable connection means (not shown) couples the sensing coil 14 to a signal measuring device.

Magnetic Assembly for Determining Positional Coordinates of Sensing Coil

Figure 3:
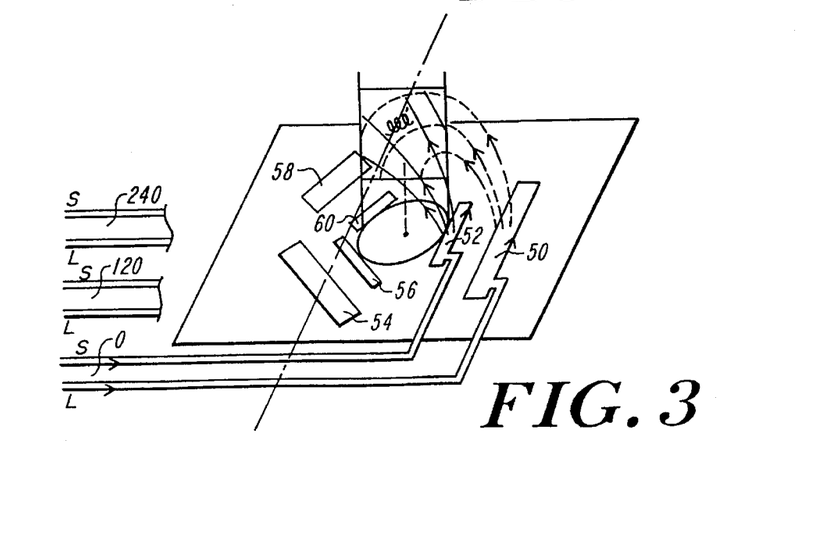
FIGS. 3 schematically illustrates a magnetic coil assembly for determining the positional coordinates of the sensing coil in accordance with a preferred embodiment of the present invention, and which is configured within the deck of FIG. 1.
Figure 5:
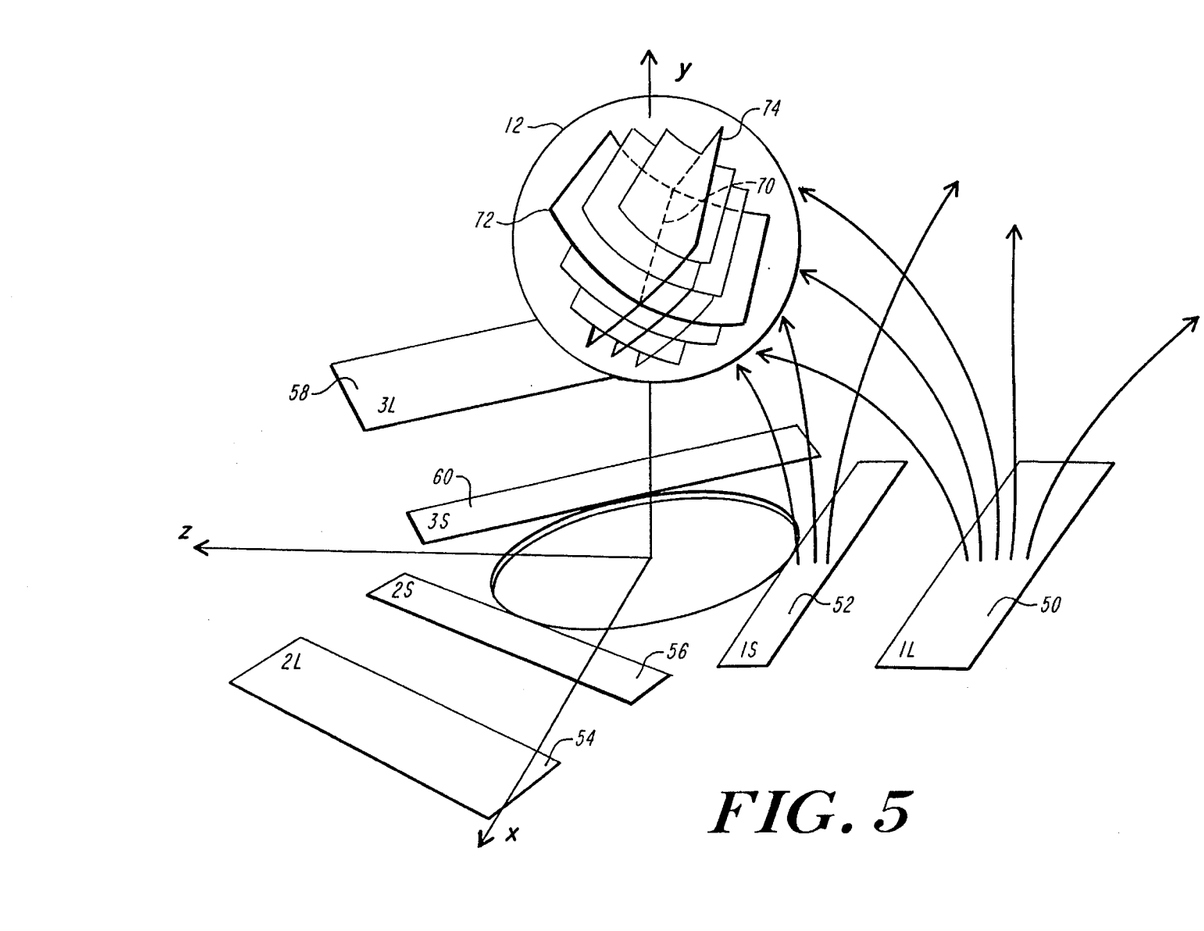
FIG. 5 schematically depicts the magnetic coil assembly of FIG. 3 to illustrate representative field patterns generated during an excitation period.

FIGS. 3 and 5 show the coil configuration used to determine the positional coordinates of the sensing coil in accordance with a preferred embodiment of the present invention. The configuration includes six coils grouped into three pairs of long and short delta coils (50–52, 54–56, 58–60). The delta coils are mutually coplanar and are disposed in the planar top of the examination deck immediately beneath the recumbent patient. Interconnection means between a signal drive unit (not shown) and the delta coil groups is shown representatively for only coils 50–52.

Figure 6:
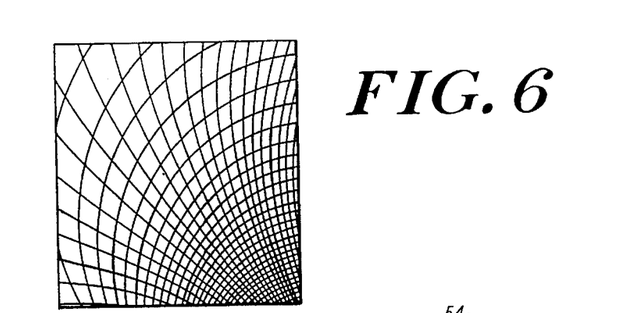
FIG. 6 is a trace representatively illustrating surfaces of constant signal from the sensing coil, as generated by the magnetic assembly of FIG. 3.

The coils are preferably arranged in a circular orientation about the y-axis such that there is an axis perpendicular to the direction of elongation of the coils at 0°, 120° and 240° relative to the z-axis. The magnetic field generated by the first group of long (50) and short delta coils (52) is shown representatively by the field lines extending from the upper region of the coils. The field lines from this delta coil group form the family of constant signal surfaces shown within the navigational domain 12. Superposition of the constant signal surfaces generated by the long and short coils of a delta coil group produces a fishnet pattern as shown in FIG. 6. The intersection of two such constant signal surfaces generated by a short and long coil pair is a single line represented by the dotted line 70.

A constant signal surface (72 and 74) is identified for each short coil and long coil activation of a delta coil pair by determining the surface that matches the induced signals developed in the sensing coil. This procedure is repeated for the other two delta coil pairs to produce two other lines comparable to line 70. The intersection of these three lines determines the position of the catheter.

Figure 7:
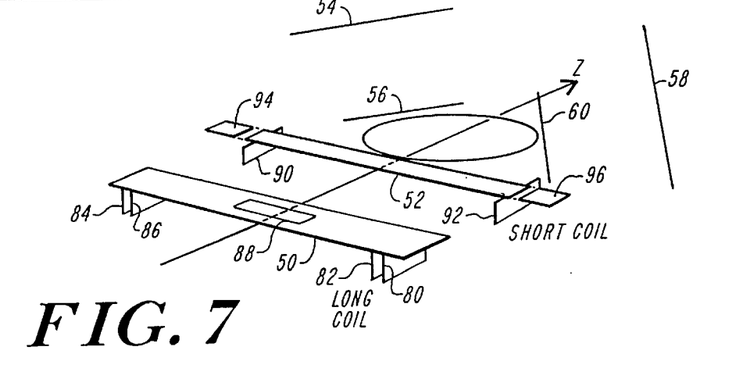
FIG. 7 shows an upper plan schematic view of the magnetic assembly of FIG. 3.

FIG. 7 shows an upper plan schematic view of the entire delta coil arrangement relative to an inner circular space representing the projection of the navigational domain into the plane of the delta coils. It is an object of the present invention to design coils having high spatial gradience in two of the axis dimensions and a substantially zero field value in the remaining axial dimension. This particular design is accomplished by modifying the termination points of the coils with compensation coils such that the modified coil is effectively operative as an infinitely long coil. The long coil sets are further compensated by a central "sucker" coil 88. Accordingly, each of the long coils and short coils is modified by representative compensation coils 80–82, 84–86, 88 and 90–94, 92–96 respectively, disposed at the indicated endpoints and center of the corresponding delta coil. The long coil and short coil configurations are shown schematically for only sets 50–52, but similar configurations likewise exist for the coil sets 54–56 and 58–60 shown representatively as the indicated lines.

The quality of the coils, as measured by the degree of uniformity of the uniform field coils or how close to zero is the field in the non-gradient direction for the delta coils, determines the size of the navigational domain over which the variable separation technique for navigating the catheter will converge and therefore be capable of initially finding the catheter, and hence be of functional utility.

Figure 8:
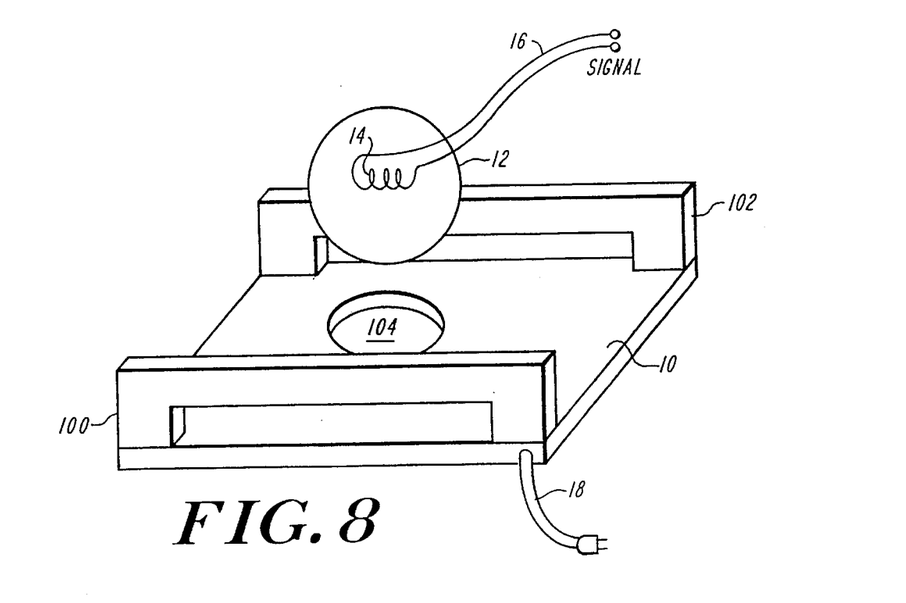
FIG. 8 schematically illustrates a perspective view of a patient-supporting examination deck in accordance with another embodiment of the present invention.

FIG. 8 schematically depicts an examination deck in accordance with another embodiment of the present invention. The deck includes a first rail member 100 and a second rail member 102 in opposed spaced-apart relationship and attached to the platform along respective supporting edges. The navigational domain is illustratively depicted as the spherical volume 12. The deck includes an apertured opening 104. Each rail member has an inner wall and an outer wall. The railed configuration is characterized by the embedding of coil sets in both the planar top and in the rail members. The examination deck is preferably constructed from a magnetically permeable material.

Figures 9A, 9B:
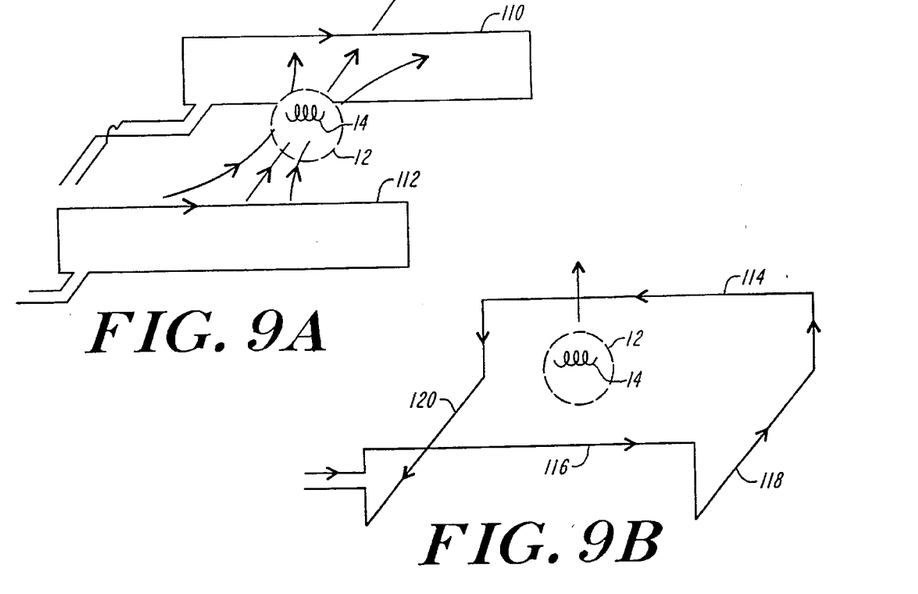
FIGS. 9A–D schematically illustrate a series of magnetic coil assemblies configured in the deck and rails of FIG. 8 for determining the orientation and position of the sensing coil in accordance with another embodiment of the present invention.
Figure 9C:
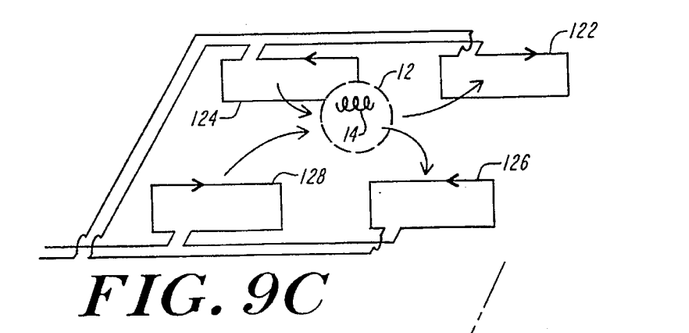
Figure 9D:
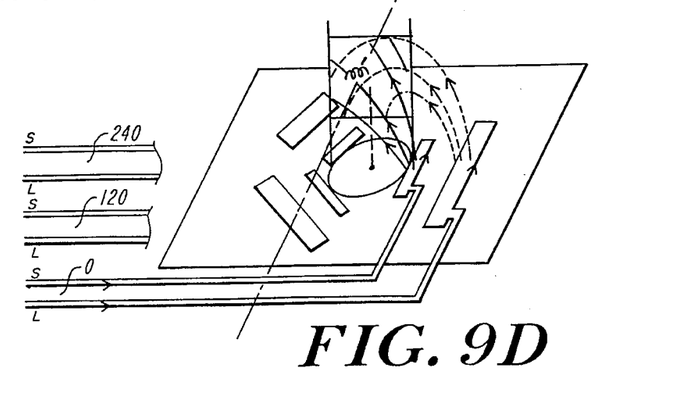

FIGS. 9A–C schematically illustrate the unidirectional coils for implementing the railed configuration used in conjunction with the examination deck of FIG. 8. The magnet assembly for the x-directed unidirectional coil set is shown in FIG. 9A and includes two coil elements 110 and 112 each embedded in a respective rail member. Each coil pair is designed to project a substantially uniform field in the x-direction throughout the navigational domain. FIG. 9B schematically depicts the y-directed unidirected coils including coil elements 114 and 116 each embedded in respective rail members, and further including coil elements 118 and 120 embedded in the planar top of the examination deck. FIG. 9C schematically depicts the z-directed unidirected coils including coil elements 122–124 in one rail member and elements 126–128 in the other rail member. The current flow through each coil configuration is indicated by the arrows. FIG. 9D shows the delta coil arrangement used in the railed configuration. This arrangement is the same as used in the flat configuration described above.

In accordance with another embodiment of the present invention, a second sensing coil is used for stabilization purposes. Inaccurate readings of the catheter probe location may occur from motion artifacts due to breathing action, heart motion, or patient movement. The stabilized location coordinates may be determined by placing a second sensing coil on the sternum of the patient at a known location within the navigational domain. The incremental movement experienced by the second sensing coil due to motion artifacts is detected and subtracted from the measured location value of the probe to arrive at the actual location coordinates of the probe. Further extensions of the present invention are possible to facilitate multi-catheter applications by attaching an additional sensing coil to the distal end of each additional catheter.

Since certain changes may be made in the above apparatus and method without departing from the scope of the invention herein described, it is intended that all matter contained in the above description or shown in the accompanying drawings shall be interpreted in an illustrative and not in a limiting sense.

What is claimed is:

1. A method of determining the location of a magnetically-sensitive, electrically conductive sensing coil affixed to a distal end of a catheter probe partially inserted into a body cavity within a navigational domain, comprising the steps of:

inducing within said sensing coil a set of orientation signal values each representative of an orientation of said sensing coil and independent of a position of said sensing coil;

determining the orientation of said sensing coil using said induced orientation signal values;

inducing within said sensing coil a set of positional signal values each representative of the position of said sensing coil; and determining the position of said sensing coil using said positional signal values and said determined orientation.

2. The method as recited in claim 1, wherein the step of inducing said set of orientation signal values comprises the steps of:

generating from outside said body a series of magnetic fields each penetrating at least said navigational domain and characterized substantially by a principal magnetic component in one axial dimension and relatively smaller magnetic components in two other axial dimensions.

3. The method as recited in claim 1, wherein the step of inducing said set of positional signal values comprises the steps of:

generating from outside said body a series of magnetic fields each penetrating at least said navigational domain and characterized substantially by two principal gradient magnetic components in respective axial dimensions and a relatively smaller magnetic components in a third axial dimension.

4. The method as recited in claim 3, wherein said generating step further includes the steps of:

generating said fields to provide a plurality of constant signal surfaces for the sensing coil such that an intersection between two such surfaces with components in the same axial dimensions produces a line along which said sensing coil is located;

wherein said two such surfaces are identified from among said plurality of constant signal surfaces by their ability to induce one of said positional signal values.

5. The method as recited in claim 4, further comprises the steps of:

weighting each line in accordance with a signal strength of said corresponding constant signal surface; and determining an intersection of said weighted lines.

6. The method as recited in claim 5, wherein six constant signal surfaces are generated to produce three intersection lines.

7. A system for determining the location of a magnetically-sensitive, electrically conductive sensing coil affixed to a distal end of a catheter probe partially inserted into a body cavity within a navigational domain, comprising:

first transmit means for projecting into said navigational domain magnetic energy that is sufficient to induce signal values within said sensing coil representative of an orientation of said sensing coil and independent of the position of said sensing coil;

second transmit means for projecting into said navigational domain magnetic energy that is sufficient to induce signal values within said sensing coil representative of the position of said sensing coil; and analysis means, coupled to said first transmit means and said second transmit means, for determining the position and orientation of said sensing coil from said induced signal values.

8. A system for determining the location of a magnetically-sensitive, electrically conductive sensing coil affixed to a distal end of a catheter probe partially inserted into a body cavity within a navigational domain, comprising:

first signal-inducing means for inducing within said sensing coil orientation signals that are representative of the orientation of said sensing coil;

analysis means, coupled to said first signal-inducing means, for determining the orientation of said sensing coil using said induced orientation signals and independent from a position of said sensing coil;

second signal-inducing means for inducing within said sensing coil position signals that are representative of the position of said sensing coil; and analysis means, coupled to said second signal-inducing means, for determining the position of said sensing coil using said determined orientation and said induced position signals.

9. The system as recited in claim 8, wherein the first signal-inducing means comprises:

field generation means for successively generating magnetic field patterns projected into said navigational domain, each characterized substantially by a principal magnetic field component in one direction and relatively smaller magnetic components in two other directions.

10. The system as recited in claim 9, wherein said field generation means comprises a set of magnetic coils.

11. The system as recited in claim 10, wherein said magnetic coils are disposed in a planar top of an examination deck upon which a patient is disposed during a surgical procedure.

12. The system as recited in claim 10, wherein said magnetic coils are disposed in a planar top and in rail members edge supported by said planar top for an examination deck upon which a patient is disposed during a surgical procedure.

13. The system as recited in claim 8, wherein the second signal-inducing means comprises:

field generation means for successively generating magnetic field patterns each characterized by a first and second gradient field component in respective directions and a relatively smaller third component in another direction.

14. The system as recited in claim 13, wherein the field generation means comprises a magnetic coil assembly.

15. A method of determining the location of a magnetically-sensitive, electrically conductive sensing coil affixed to a distal end of a catheter probe partially inserted into a body cavity within a navigational domain, comprising the steps of:

defining the location of said sensing coil with a set of independent location parameters; and sequentially generating within said navigational domain a sequence of magnetic fields for inducing within said sensing coil a corresponding sequence of induced signals each defined by an induced signal expression that functionally relates said induced signal to certain ones of said location parameters, such that said set of location parameters is determinable by sequentially solving individual signal expression groups each including certain ones of said induced signal expressions and sufficient to represent a subset of said location parameters.

16. The method as recited in claim 15, wherein said sequence of magnetic fields comprises:

a series of unidirectional magnetic fields each characterized substantially by a principal magnetic field component in one direction and relatively smaller magnetic components in two other directions; and a series of gradient magnetic fields each characterized by a first and second gradient field component in respective directions and a relatively smaller third component in another direction.

17. The method as recited in claim 16, wherein said signal expression groups include:

an orientation group including induced signal expressions each functionally related to a respective one of said unidirectional magnetic fields and an orientation of said sensing coil, and independent of a position of said sensing coil; and a position group including induced signal expressions each functionally related to a respective one of said gradient magnetic fields, the orientation of said sensing coil, and the position of said sensing coil.

18. The method as recited in claim 17, wherein the step of sequentially solving said individual signal expression groups includes the steps of:

initially solving the induced signal expressions of said orientation group; and next solving the induced signal expressions of said position group.

19. A system for determining the location of a magnetically-sensitive, electrically conductive sensing coil affixed to a distal end of a catheter probe partially inserted into a body cavity within a navigational domain, comprising:

means for defining the location of said sensing coil with a set of independent location parameters; and field generation means for sequentially generating within said navigational domain a sequence of magnetic fields for inducing within said sensing coil a corresponding sequence of induced signals each defined by an induced signal expression that functionally relates said induced signal to certain ones of said location parameters, such that said set of location parameters is determinable by sequentially solving individual signal expression groups each including certain ones of said induced signal expressions and sufficient to represent a subset of said location parameters.

20. The system as recited in claim 19, wherein said sequence of magnetic fields comprises:

a series of unidirectional magnetic fields each characterized substantially by a principal magnetic field component in one direction and relatively smaller magnetic components in two other directions; and a series of gradient magnetic fields each characterized by a first and second gradient field component in respective directions and a relatively smaller third component in another direction.

21. The system as recited in claim 20, wherein said signal expression groups include:

an orientation group including induced signal expressions each functionally related to a respective one of said unidirectional magnetic fields and an orientation of said sensing coil, and independent of a position of said sensing coil; and a position group including induced signal expressions each functionally related to a respective one of said gradient magnetic fields, the orientation of said sensing coil, and the position of said sensing coil.

22. The system as recited in claim 21, wherein said field generation means comprises:

analysis means for solving the induced signal expressions of said orientation group; and analysis means for solving the induced signal expressions of said position group.

* * * * *

UNITED STATES PATENT AND TRADEMARK OFFICE
Certificate

Patent No. 5,592,939                                         Patented: January 14, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael A. Martinelli, Winchester, MA; and Wayne C. Haase, Sterling, MA.

Signed and Sealed this Thirty-first Day of August 2004.

BRIAN CASLER
*Supervisory Patent Examiner*
Art Unit 3763